US007015222B1

(12) United States Patent
Koppes et al.

(10) Patent No.: US 7,015,222 B1
(45) Date of Patent: Mar. 21, 2006

(54) AGRICULTURAL COMPOSITIONS

(75) Inventors: William M. Koppes, Adelphi, MD (US); Michael E. Sitzmann, Adelphi, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/781,956

(22) Filed: Feb. 20, 2004

Related U.S. Application Data

(63) Continuation-in-part of application No. 10/439,804, filed on May 19, 2003, which is a continuation-in-part of application No. 10/171,114, filed on Jun. 14, 2002, now Pat. No. 6,632,305, which is a continuation-in-part of application No. 09/874,946, filed on Jun. 6, 2001, now Pat. No. 6,423,844.

(51) Int. Cl.
C07D 487/04 (2006.01)
A61K 31/53 (2006.01)

(52) U.S. Cl. ............... 514/241; 544/198; 544/209
(58) Field of Classification Search ............ 544/198, 544/209; 514/241
See application file for complete search history.

(56) References Cited

U.S. PATENT DOCUMENTS

| 2,473,797 A | 6/1949 | Kaiser et al. ............ 260/249.5 |
| 2,475,440 A | 7/1949 | Walter ...................... 260/239 |
| 3,061,605 A | 10/1962 | D'Alelio .................. 260/239.7 |
| 3,725,067 A | 4/1973 | Bailey et al. ............... 96/56.5 |
| 3,758,309 A | 9/1973 | Bailey et al. ................. 96/136 |
| 3,939,084 A | 2/1976 | Sullivan ................... 252/47.5 |
| 4,236,003 A | 11/1980 | Fletcher .................... 544/254 |
| 4,549,018 A | 10/1985 | Siedle ....................... 544/225 |
| 4,565,815 A | 1/1986 | Kim et al. .................. 514/246 |
| 4,621,046 A | 11/1986 | Sato et al. .................. 430/381 |

OTHER PUBLICATIONS

Article: "The Synthesis and Dimroth-Type Rearrangement of 5,7-Bis(dimethylamino)-3-(methylthio)-s-triazolo[4,3-a]-s-triazine", DeMilo et al., J. Heterocyclic Chem. 10, 231 (Apr. 1973), pp 231-233.
Article: "New Synthesis of Dyes of the Triazine", Series II. VAT Dyes of the Triazolo-Triazine Series by A. Titkov and I.D. Pletnev, Scientific Research Institute of Intermediates and Dyes, translated from Zhurnal Obshchel Khimil, vol. 33, No. 4, pp. 1355-1357, Apr. 1963.
Abstract: No. 93042a Basic azo dye. Maeda, Hhigeo et al. (40-Dyes, vol. 81, 1974), referencing Maeda et al. Japan Kokai 74 24,226.
Abstract: No. 122766x Basic azo dye. Maeda, Hhigeo et al. (40-Dyes, vol. 81, 1974), referencing Maeda et al. Japan Kokai 74 27,287.
Article: "Chemistry ofDicyandiamide V Structures of Guanazo- and Pyro-Guanazoles, and Reaction of Dicyandiamide with 3-Amino-5-Substituted-1,2,4,4H-Triazoles", kaiser et al. J. Organic Chemistry, vol. 18, 1953, pp. 1610-1614.

*Primary Examiner*—Venkataraman Balasubramanian
(74) *Attorney, Agent, or Firm*—Fredric J. Zimmerman

(57) ABSTRACT

An agricultural composition comprising the chemical formula, or salt thereof, of:

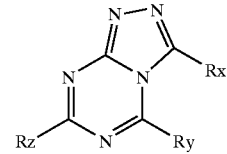

wherein Rx is —$NH_2$, —OH, halogen, akylamino, $SR_1$, carboxyalkyl, carboxy, or a sulfonamide moiety, wherein $R_1$ is a H or a $C_1$ to $C_6$ alkyl moiety, and Ry and Rz, independently, are electron donating groups and an agriculturally acceptable carrier.

19 Claims, No Drawings

AGRICULTURAL COMPOSITIONS

This application is a continuation-in-part (CIP) of U.S. patent application Ser. No. 10/439,804, entitled "Colorant Compostions", filed May 19, 2003, which is a continuation-in-part (CIP) of U.S. patent application Ser. No. 10/171,114, entitled "1,2,4-Triazolo[4,3-a][1,3,5] Triazine-3,5,7-Substituted Precursor, and Process, and Compounds Therefrom", filed Jun. 14, 2002, now U.S. Pat. No. 6,632,305, issued Oct. 12, 2003, which is a continuation-in-part (CIP) of U.S. patent application Ser. No. 09/874,946, entitled "Process for Making 1,2,4-Triazolo[4,3-a][1,3,5] Triazine-3,5,7-Triamine", filed Jun. 6, 2001, now U.S. Pat. No. 6,423,844, issued Jul. 23, 2002.

STATEMENT OF GOVERNMENT INTEREST

The invention described herein may be manufactured and used by or for the Government of the United States of America for governmental purposes without payment of any royalties thereon or therefor.

BACKGROUND OF THE INVENTION

1. Field of the Invention

The present invention pertains to novel triazolyl-triazine agricultural compositions.

2. Brief Description of the Related Art

Development of specialized chemical compounds requires proper precursor chemical structures. Current methods that purport to synthesize 1,2,4-triazolo[4,3-a][1,3,5] triazine-3,5,7-triamine all involve heating dicyandiamide and hydrazine dihydrochloride at elevated temperatures (100° C. or higher) for significant amounts of time in order to condense the dicyandiamide. This method was described by Kaiser et al. in a paper published in the Journal of Organic Chemistry, Vol. 18, 1953, page 1610.

Using this synthesis method theoretically provides for two possible isomeric structures of triazolotriazinetriamine (see I and II below). The first structure is the [4,3-a]triazolotriazinetriamine, pictured below as I. The second structure is the [1,5-a]triazolotriazinetriamine, pictured below as II. The product by Kaiser et al., resulting from the method above, was assigned the structure of I based upon degradation/oxidation studies of the product. However, these types of studies provide for a large degree of uncertainty as to structure.

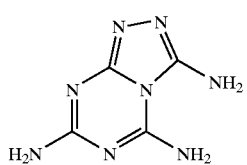

I

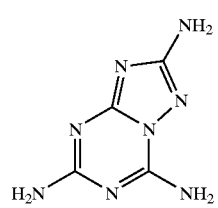

II

Recently, product derived from the above process was tested using X-ray diffraction, an extremely reliable technique, and, rather than the expected product I as originally reported, it was found that the actual structure of the product was that of II. The commercial product based upon the above method, sold under the names 3,5,7-triamino-s-triazolo[4,3-a]-s-triazine or 3,5,7-triamino-1,2,4-triazolo[4,3-a]-1,3,5-triazine, has also been tested via X-ray diffraction and found to be the structure of II. Because of the above error, prior to the present invention, there is, therefore, no known process of synthesizing product I. Additionally, patents such as U.S. Pat. No. 3,939,084 to Sullivan purport to use a 3,5,7-Triamino-s-trizazolo (4,3-a)-s-triazine, as well as articles such as "New Synthesis of Dyes of the Triazine", Series II. VAT Dyes of the Triazolo-Triazine Series by A. Titkov and I. D. Pletnev, Scientific Research Institute of Intermediates and Dyes, translated from Zhurnal Obshchel Khimil, Vol. 33, No. 4, pp. 1355–1357, April 1963 (see also Maeda et al. Japan Kokai 74 24,226 and 74 27,287), are apparent mislabelings of the 3,5,7-Triamino-s-triazolo (1,5-a)-s-triazine.

The effects of the structural difference between these two products on the chemical and physical properties are of interest in any application of monotriazolotriazine ring systems. Of particular interest for energetic uses of these products would be the energy release in detonation, which correlates to the density of the materials. An analysis of densities and potential energy releases of the products reveals that the product I has a higher potential energy release value than product II that is significant in defense related energetic systems. The product II has also been investigated for use in the dye industry as a chromophore coupled to anthraquinones and indoles, and, therefore, product I should have similar potential uses. Other aromatic structure systems also are of interest.

Due to the discovery that the chemical sold as product I is actually product II, and the chemical and physical properties of the two products are significant for many uses, it would be desirable to derive product I, and like compounds, provide for synthesis such compounds, as well as developing compounds from processes using product I and like compounds as a precursor.

SUMMARY OF THE INVENTION

The present invention includes an agricultural composition comprising the chemical formula, or salt thereof, of:

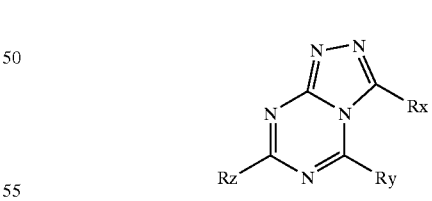

wherein Rx is —$NH_2$, —OH, halogen, akylamino, $SR_1$, carboxyalkyl, carboxy, or a sulfonamide moiety, wherein $R_1$ is a H or a $C_1$ to $C_6$ alkyl moiety, and Ry and Rz, independently, are electron donating groups and an agriculturally acceptable carrier.

The present invention also includes a process for producing an agricultural composition, comprising the steps of forming an agricultural composition having the above-identified chemical formula, wherein Rx is —$NH_2$, and adding an agriculturally acceptable carrier thereto. In a second preferred embodiment, Rx, i.e., —NH$_2$, is replaced with an agriculturally effective substituent prior to adding the agriculturally acceptable carrier.

Additionally, the present invention includes treated agricultural products, particularly for insecticidal, fungicidal or herbicidal treatment.

DETAILED DESCRIPTION OF THE INVENTION

The present invention includes an agricultural composition comprising the chemical formula, or salt thereof, of:

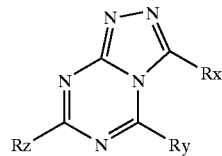

wherein Rx is —NH$_2$, —OH, halogen, akylamino, SR$_1$, carboxyalkyl, carboxy, or a sulfonamide moiety, wherein R$_1$ is a H or a C$_1$ to C$_6$ alkyl moiety, and Ry and Rz, independently, are electron donating groups and an agriculturally acceptable carrier.

The present invention may be made by a process for making a 1,2,4-triazolo[4,3-a][1,3,5]triazine-3,5,7-substituted compound, acid salt, particularly 1,2,4-triazolo[4,3-a][1,3,5]triazine-3,5,7-triamine, acid salt and a process for neutralizing the acid salt to make a 1,2,4-triazolo[4,3-a][1,3,5]triazine-3,5,7-substituted compound, particularly 1,2,4-triazolo[4,3-a][1,3,5]triazine-3,5,7-triamine, providing a product of this process (the 1,2,4-triazolo[4,3-a][1,3,5]triazine-3,5,7-substituted compound, including the 1,2,4-triazolo[4,3-a][1,3,5]triazine-3,5,7-triamine is referred to herein as the "precursor"). Because of the reactive properties of the precursor, this precursor is useful in deriving compounds for agricultural use.

The general process involves ring closure of a 2,4-substituted diamino-6-hydrazino-s-triazine with an acid and a chemical of the general formula RCN where the R comprises a leaving group, and then neutralizing said acid. Because the hydrazine nitrogen atoms that form the triazole ring are already in place on the 2,4-substituted-6-hydrazino-s-triazine, the final product formed is the desired [4,3-a] isomer, rather than the [1,5-a]isomer produced by the conventional dicyandiamide/hydrazine dihydrochloride methods. The general formulas for the process are set forth below:

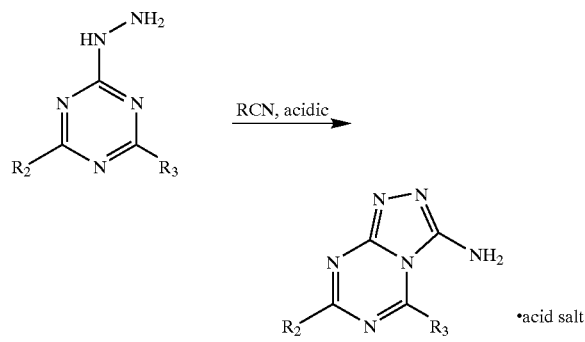

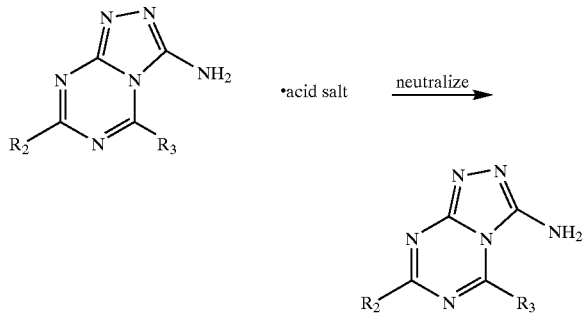

wherein the R comprises a leaving group, and R$_2$ and R$_3$ comprise electron donating groups.

More specifically, first, the invention comprises a process for the preparation of 1,2,4-triazolo[4,3-a][1,3,5]triazine-3,5,7-substituted compound, acid salt, with an amino group at the 3-position. In order to practice the present invention, one may first obtain or synthesize 2,4-diamino-6-hydrazino-s-triazine. One method for synthesizing this chemical is set forth in U.S. Pat. No. 3,061,605 by D'Alelio. The general method is to effect a reaction between 2,4-diamino-6-chloro-1,3,5-triazine and hydrazine. A specific example is set forth in column 3, lines 60–70 of the above patent and are hereby incorporated by reference. While this particular method of synthesizing 2,4-diamino-6-hydrazino-s-triazine is specifically disclosed, any prior art method of synthesis would be appropriate to practice the present invention.

The first step in the present invention comprises dissolving the 2,4-diamino-6-hydrazino-s-triazine with an acid. This step is preferably carried out at room temperature with an acid that is of sufficient strength to dissolve the 2,4-diamino-6-hydrazino-s-triazine. Many acids can be employed in the present invention, such as sulfuric acid or hydrochloric acid or mixtures of these acids with other solvents such as methanol or ethanol, and may be selected by one skilled in the art. One preferred acid is 1N hydrochloric acid.

The second step comprises mixing the dissolved 2,4-diamino-6-hydrazino-s-triazine with a reagent of the formula RCN, wherein R comprises a leaving group. This reaction will provide the amino triazole ring on the product directly. A leaving group, as used in this application, is a group that can be displaced to give ring closure; that is, produces the amino triazole ring. One preferred leaving group comprises bromine wherein the reagent comprises cyanogen bromide. Although the reaction in this step is acid catalyzed, preferred reaction times range from about twenty hours to about thirty hours in order to allow for the maximum formation of acid salt crystals. It is also preferred that the acid salt crystals be removed after the reaction is substantially complete, approximately thirty hours, to prohibit contamination of the final product with impurities. The crystals may be removed by any normal method, such as filtration, and can then be washed and dried in order to obtain the final acid salt product.

The present invention also comprises a process to take the 1,2,4-triazolo[4,3-a][1,3,5]triazine-3,5,7-triamine, acid salt synthesized above, and neutralize the acid salt crystals in order to obtain a final product of 1,2,4-triazolo[4,3-a][1,3,5]triazine-3,5,7-triamine. This process involves the steps described above as well as the following steps.

First, the acid salt crystals are removed from the solution synthesized above. Then, the acid salt crystals are neutralized by mixing them with a substance more basic than 1,2,4-triazolo[4,3-a][1,3,5]triazine-3,5,7-triamine. This step results in the removal of the acid from the above reaction and provides for a final product of 1,2,4-triazolo[4,3-a][1,3,5]triazine-3,5,7-triamine. The substance used in this final step may be selected by one skilled in the art based upon the basicity of the substance versus the basicity of 1,2,4-triazolo[4,3-a][1,3,5]triazine-3,5,7-triamine. Some examples are potassium carbonate, potassium acetate, sodium bicarbonate, and sodium hydroxide. One preferred substance is potassium carbonate. It is also preferred that the reaction take place in solution, so preferably, water or some other solvent may be added to the salt.

Due to the reactive nature of the —NH$_2$ from the five-member ring, derivatives of the precursor, the —NH$_2$ may be readily replaced with a separate agriculturally effective substituent, useful in a wide range of agricultural areas, including for example, agricultural compositions, such as without limitation herbicides, pesticides, fungicides and/or fertilizers. For example, triazoles and/or triazines are known in the fields of agriculture (see e.g., U.S. Pat. No. 5,602,075 to Benko et al., herbicides) and agricultural chemicals, medicines, dyes, paints, and the like, as various resin materials, such as aminoplast molded materials and flame retarding materials (see e.g., U.S. Pat. No. 6,127,538 to Tanaka et al.; see col. 1, lns. 26–30; see also U.S. Pat. No. 5,371,218 to Cipolli et al.). Agriculturally effective substituents preferably include H, —OH, halogen, alkylamino, SR$_1$, carboxyalkyl, or carboxy, wherein R$_1$ is H or a C$_1$ to C$_6$ alkyl moiety. Representative agriculturally effective substituents include, for example, H, COOEt, SH and —OH, SR$_1$, —NH$_2$ or a halogen, with —NH$_2$ or a halogen preferred, and —NH$_2$ or —Cl more preferred. In one preferred embodiment, Rx is a agriculturally effective sulfonamide substituent.

Additionally a highly active insect sterilant, 2,4,6-tris(dimethylamino)-s-triazine is disclosed in DeMilo, Albert B., James E. Oliver and Richard D. Gilardi, "The Synthesis and Dimroth-Type Rearrangement of 5,7-Bis(dimethylamino)-s-(methylthio)-s-triazolo [4,3-α]s-triazine", J. Heterocyclic Chem. 10, 231 (1973), the disclosure of which is herein incorporate by reference.

As used herein, an "electron donating group" designates a group that will release or donate electrons more than hydrogen would if it occupied the same position in the molecule. See J. March, Advanced Organic Chemistry, 3$^{rd}$ Ed., John Wiley & Sons p. 238 (1985). These types of groups are well known in the art. Examples of Ry and Rz, independently, preferably include electron donating groups such as lower alkylamino, di-loweralkylamino, amino, hydroxy, carboxy, aryl, lower alkoxy, lower aralkoxy, aryloxy, mercapto and lower alkylthio. More preferably Ry and Rz, independently, are electron donating groups selected from the group consisting of —O—, —COO—, —OR, —CR$_A$R$_B$R$_C$, —OCOR, —NR$_A$R$_B$, SR, wherein R and R$_{A\text{-}C}$ are independently an alkyl group or H. R may include a C$_1$ to C$_6$ alkyl moiety, C$_1$ to C$_4$ alkyl moiety, C$_1$ to C$_3$ alkyl moiety or C$_1$ alkyl moiety. R and R$_{A\text{-}C}$ preferably include one of H, CH$_3$, —CH$_2$CH$_3$, —CH(CH$_3$)$_2$ and —CH(CH$_2$CH$_3$)$_2$. Representative Ry and Rz components include, for example, —NH$_2$, —CH$_3$, —OCH$_3$, —NHCH$_3$, —N(CH$_3$)$_2$, —N(CH$_3$)(CH$_2$CH$_3$), —N(CH$_2$CH$_3$)$_2$, —NH(CH$_2$CH$_3$) and —NH(CH(CH$_3$)$_2$). It is noted that in a diazotization reaction, when Ry is amino, there is the possibility of a competing reaction to form a tetrazine ring.

PRECURSOR

The precursor comprises a 1,2,4-triazolo[4,3-a][1,3,5]triazine-3,5,7-triamine, acid salt or its neutralized form of 1,2,4-triazolo[4,3-a][1,3,5]triazine-3,5,7-triamine. The general process involves ring closure of 2,4-diamino-6-hydrazino-s-triazine with an acid and a chemical of the general formula RCN where the R comprises a leaving group, and then neutralizing the acid.

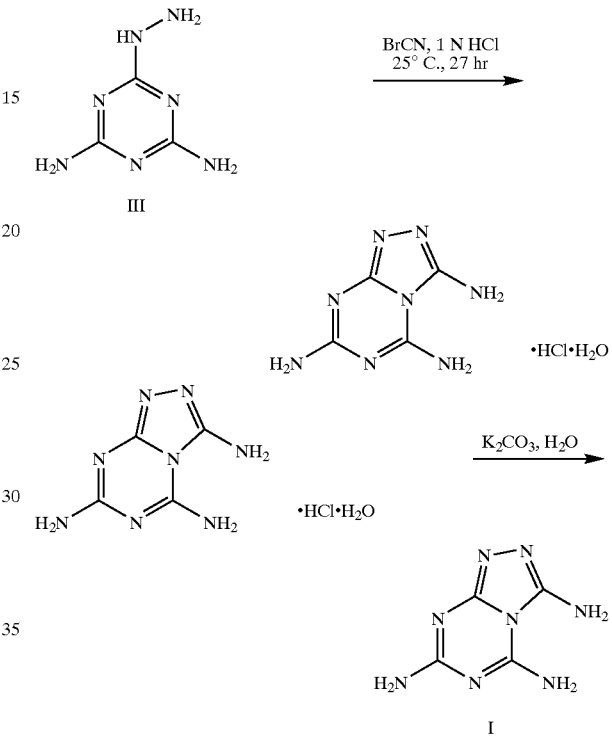

The structure of the precursor is shown below:

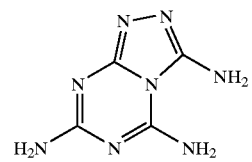

More specifically, the 1,2,4-triazolo[4,3-a][1,3,5]triazine-3,5,7-triamine, acid salt is derived first by obtaining or synthesizing 2,4-diamino-6-hydrazino-s-triazine. One method for synthesizing this chemical is set forth in U.S. Pat. No. 3,061,605 by D'Alelio. The general method is to effect a reaction between 2,4-diamino-6-chloro-1,3,5-triazine and hydrazine. A specific example is set forth in column 3, lines 60–70 of the above patent which is hereby incorporated by reference. While this particular method of synthesizing 2,4-diamino-6-hydrazino-s-triazine is specifically disclosed, any prior art method of synthesis would be appropriate to practice the present invention. The 2,4-diamino-6-hydrazino-s-triazine is dissolved with an acid, preferably out at room temperature with an acid that is of sufficient strength to dissolve the 2,4-diamino-6-hydrazino-s-triazine. Many acids can be employed in the present invention, such as sulfuric acid or hydrochloric acid or mixtures of these acids with other solvents such as methanol or ethanol, and may be selected by one skilled in the art. One preferred acid is 1N hydrochloric acid. The dissolved 2,4-diamino-6-hydrazino-s-triazine is mixed with a reagent of the formula RCN, wherein R comprises a leaving group. This reaction will provide the amino triazole ring on the product directly. A leaving group, as used in this application, is a group that can be displaced to give ring closure; that is, produces the amino triazole ring. One preferred leaving group comprises bromine wherein the reagent comprises cyanogen bromide. Although the reaction in this step is acid catalyzed, preferred reaction times range from about twenty hours to about thirty hours in order to allow for the maximum formation of acid salt crystals. It is also preferred that the acid salt crystals be removed after the reaction is substantially complete, approximately thirty hours, to prohibit contamination of the final product with impurities. The crystals may be removed by any normal method, such as filtration, and can then be washed and dried in order to obtain the final acid salt product.

Neutralization of the 1,2,4-triazolo[4,3-a][1,3,5]triazine-3,5,7-triamine, acid salt crystals synthesized above to obtain a final product of 1,2,4-triazolo[4,3-a][1,3,5]triazine-3,5,7-triamine is accomplished by mixing the crystals with a substance more basic than 1,2,4-triazolo[4,3-a][1,3,5]triazine-3,5,7-triamine. This step results in the removal of the acid from the above reaction and provides for a final product of 1,2,4-triazolo[4,3-a][1,3,5]triazine-3,5,7-triamine. The substance used in this final step may be selected by one skilled in the art based upon the basicity of the substance versus the basicity of 1,2,4-triazolo[4,3-a][1,3,5]triazine-3,5,7-triamine. Some examples are potassium carbonate, potassium acetate, sodium bicarbonate, and sodium hydroxide. One preferred substance is potassium carbonate. It is also preferred that the reaction take place in solution, so preferably, water or some other solvent may be added to the salt.

The following examples (Examples 1A–1C) are preparations of the 1,2,4-triazolo[4,3-a][1,3,5]triazine-3,5,7-triamine precursors, with the chemical structures shown below:

EXAMPLE 1A

Prep. of 1,2,4-triazolo[4,3-a][1,3,5]triazine-3,5,7-triamine, hydrochloric salt hydrate To 126 g of 1 N hydrochloric acid stirred at 25° C. was added 9.06 g (0.0570 mole) of 2,4-diamino-6-hydrazino-s-triazine [prepared according to G. F. D'alelio, U.S. Pat. No. 3,061,605 (1962), which is incorporated herein by reference]. The mixture was stirred for 10 minutes, at which time nearly all of the 2,4-diamino-6-hydrazino-s-triazine had dissolved. Cyanogen bromide (9.3 g, 0.0877 mole) was added at one time and, after 5 minutes, all of the material was in solution. After about 1 hour, crystals began to precipitate. After 3 hours, stirring was stopped and the mixture was allowed to stand for an additional 24 hours to continue precipitation of crystals. The crystals were removed by filtration and washed with 2× 25 ml cold water. The crystals were air dried and then dried in a vacuum desiccator over Drierite to give 8.60 g (68.4% yield) of product. IR (KBr): 3300, 3155, 1708, 1695, 1624, 1534, 1490, 1444, 1339, 1173, 1073, 979, 845, 772 cm$^{-1}$. Anal. Calcd for $C_4H_6N_8$ (HCl) ($H_2O$): C, 21.77; H, 4.11; N, 50.79; Cl, 16.07. Found: C, 21.84; H, 4.25; N, 50.02; Cl, 16.02.

EXAMPLE 1B

Prep. of 1,2,4-triazolo[4,3-a][1,3,5]triazine-3,5,7-triamine

To 6.86 g (0.031 mole) of 1,2,4-triazolo[4,3-a][1,3,5]triazine-3,5,7-triamine, hydrochloric salt hydrate stirred in 175 ml of water was added 4.40 g (0.031 mole) of potassium carbonate and the mixture was stirred vigorously for 40 minutes. The solid was removed by filtration, washed with water, and dried to give 4.83 g (94%) of 1,2,4-triazolo[4,3-a][1,3,5]triazine-3,5,7-triamine. $^{13}$C NMR ($CD_3CO_2D/D_2O$, 1:1 by vol): 145.7, 151.1, 151.9, 164.0. $^{13}$C NMR ($D_2SO_4$): 133.6, 141.9, 143.1, 149.5. IR (KBr): 3413, 3314, 3096, 1654, 1611, 1540, 1480, 1430, 1375, 979, 859, 770 cm$^{-1}$. Anal. Calcd for $C_4H_6N_8$: C, 28.92; H, 3.64; N, 67.44. Found: C, 28.64; H, 3.65; N, 66.08.

EXAMPLE 1C

Prep. of 1,2,4-triazolo[4,3-a][1,3,5]triazine-3,5,7-triamine, hydrochloric salt hydrate To 0.31 g (0.003 mole) of 37% hydrochloric acid in water (4 ml) and methanol (21 ml) stirred at 25° C. was added 0.42 g (0.003 mole) of 2,4-diamino-6-hydrazino-s-triazine [prepared according to G. F. D'alelio, U.S. Pat. No. 3,061,605 (1962)]. Cyanogen bromide (0.32 g, 0.003 mole) was then added at one time. The solution was held at 77–80° C. for 3 hours, before it was cooled to 25° C. and a small amount of solid was removed by filtration. The volatiles were removed from the filtrate to give 0.60 g of solid that was mainly 1,2,4-triazolo[4,3-a][1,3,5]triazine-3,5,7-triamine, hydrochloric salt hydrate by TLC and IR analyses.

Examples 1A and 1C

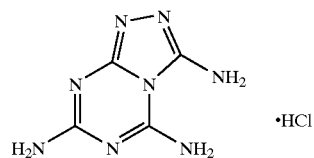

Example 1B

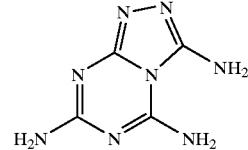

EXAMPLE 2

Prophetic

Aminotriazolo-disubstituted($R_z$, $R_y$)triazine, hydrochloric acid salt crystals are stirred with cold aqueous sodium nitrite to produce the diazonium salt ($R_x=N_2^+$). The diazonium salt mixture is poured into cold cuprous chloride/hydrochloric acid solution and the mixture is slowly heated to decompose the diazonium salt and produce the chlorotriazolo-disubstituted($R_z$, $R_y$)triazine product ($R_x=Cl$).

EXAMPLE 3

Prophetic

Aminotriazolo-disubstituted($R_z$, $R_y$)triazine, acid salt crystals are neutralized and then reacted in an inert solvent with an appropriate sulfonyl choride, e.g., benzenesulfonyl chloride (in the presence of a hydrogen ion acceptor such as pyridine or triethylamine). The triazolo-disubstituted($R_z$, $R_y$)triazine sulfonamide product (e.g., $R_x$=NHSO$_2$C$_6$H$_5$) is isolated and washed with water to remove salts of the hydrogen ion acceptor.

EXAMPLE 4

Prophetic

Aminotriazolo-disubstituted($R_z$, $R_y$)triazine, acid salt crystals are stirred with cold aqueous sodium nitrite to produce the diazonium salt ($R_x$,=N$_2^+$). The diazonium salt mixture is poured into cold cuprous cyanide solution and the mixture is slowly heated to decompose the diazonium salt and produce the cyanotriazolo-disubstituted($R_z$, $R_y$)triazine product (R=CN).

The cyano group in the cyanotriazolo-disubstituted($R_x$, $R_y$)triazine product is hydrolyzed using standard conditions (using an acid catalyst) to produce a carboxytriazolo-disubstituted($R_z$, $R_y$)triazine ($R_x$=COOH).

Standard esterification procedures are used on the carboxytriazolo compound to produce a carboxyester, e.g., carboxyethyl ($R_x$=COOEt).

EXAMPLE 5

Prophetic

Aminotriazolo-disubstituted($R_x$, $R_y$)triazine, acid salt crystals are stirred with cold aqueous sodium nitrite to produce the diazonium salt ($R_x$=N$_2^+$). The diazonium salt mixture is poured into cold sodium hydrosulfide solution and the mixture is slowly heated to decompose the diazonium salt and produce the triazolo-disubstituted($R_x$, $R_y$)triazine thiol ($R_x$=SH).

The above-identified chemical formula is processed into an agricultural composition by forming the chemical formula, or salt thereof, and adding an agriculturally acceptable carrier thereto. Agriculturally acceptable carriers include adjuvants, mixers, enhancers, etc. beneficial for application of the chemical formula. Suitable carriers should not be phytotoxic to valuable crops, particularly at the concentrations employed in applying the compositions for selective weed control in the presence of crops, and should not react chemically with the compounds of the chemical formula herein or other composition ingredients. Such mixtures can be designed for application directly to weeds or their locus or can be concentrates or formulations which are normally diluted with additional carriers and adjuvants before application. They may include inert or active components and can be solids, such as, for example, dusts, granules, water dispersible granules, or wettable powders, or liquids, such as, for example, emulsifiable concentrates, solutions, emulsions or suspensions. Suitable agricultural carriers useful in preparing agricultural compositions of the present invention are well known to those skilled in the art. For example, liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates. Suitable solid carriers include talc, pyrophyllite clay, silica, attapulgus clay, kieselguhr, chalk, diatomaceous earth, lime, calcium carbonate, bentonire clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or non-ionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzene-sulfonate; alkylphenol-alkylene oxide addition products, such as nonylphenol-C.sub.18 ethoxylate; alcohol-alkylene oxide addition products, such as tridecyl alcohol-C.sub.16 ethorylate; soaps, such as sodium stearate; alkylnaphthalene-nesulfonate salts, such as sodium dibutylnaphthalene-sulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorants, penetrations aids, spreading agents, sticking agents, dispersing agents, thickening agents, freeze point depressants, antimicrobial agents, and the like. The compositions can also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the agricultural compositions of the present invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.001 to about 5 weight percent active ingredient and preferably contain about 0.01 to about 0.5 percent.

The present compositions can be applied to weeds or their locus by the use of conventional ground or aerial dusters, sprayers, and granule applicators, by addition to irrigation water, and by other conventional means known to those skilled in the art.

The present invention may be useful as preemergence and postemergence compositions. They can be employed at non-selective (higher) rates of application to control essentially all of the vegetation, fungal, or insects in an area and, often, at selective (lower) rates of application for the selective control of undesirable infestations in grass crops, such as corn, wheat, barley, and rice as well as in broadleaf crops, such as soybeans and cotton. The present invention provides treatment in any appropriate composition, particularly as insecticidal, fungicidal or herbicidal treatment. The term "fungicide" includes any agent which destroys fungi and/or inhibits their growth and is generally used on farm crops, preferably as a protective treatment rather than a curative treatment, by application to the surface of the plant in water suspensions or dusts before attack of a fungus. The term "herbicide" includes any agent which destroys and/or inhibits the growth of undesirable plants and can be used in a preplanting, preemergence, postemergence or sterilant application. The term "insecticide" includes any agent used primarily for the control of insects by preventing, destroying, repelling or mitigating any insects which may be present in any environment whatsoever. These terms include the concepts of "acaricide" (agent used primarily in the control of plant-feeding mites, especially spider mites), "nematicide" (agent used primarily for the control of root-infesting nematodes on crop plants), "insect pheromone" (agent used primarily for the control of behavioral responses of insects), "rodenticide" (agent used primarily for the control of rodents, such as rats, mice, etc., and related animals such as rabbits), "biocide" (agent used primarily to protect inanimate materials or industrial processes from biodeterioration by microorganisms and includes classes of compounds comprising microbicides, preservatives, disinfectants and antiseptics) and "microbicide" (includes compounds that are bactericides, fungicides, algicides, molluscicides and slimicides).

Most particularly, the present invention provides a herbicidal active ingredient which controls or adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation are meant to include germinant seeds, emerging seedlings and established vegetation, as well as marine vegetation. Herbicidal activity is exhibited by the compounds of the present invention when they are applied directly to the plant or to the locus of the plant at any stage of growth or before emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote selective treatments.

The foregoing summary, description, and examples of the invention are not intended to be limiting, but are only exemplary of the inventive features which are defined in the claims.

What is claimed is:

1. A triazolyl-triazine composition, comprising:
a compound of chemical formula, or salt thereof, of

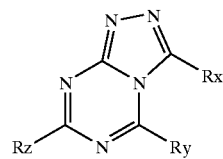

wherein Rx is selected from —NH$_2$, —OH, halogen, alkylamino, carboxyalkyl, carboxy, and a sulfonamide moiety, and
wherein Ry and Rz, independently, are electron donating groups; and, an agriculturally acceptable carrier, wherein said agriculturally acceptable carrier is selected from at least one of adjuvants, mixers, and enhancers to benefit application of said chemical formula, or said salt thereof.

2. An agricultural composition, comprising:
a compound of chemical formula, or a salt thereof, of

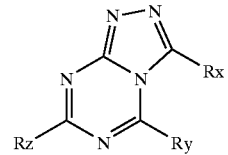

wherein Rx is selected from —NH$_2$, —OH, halogen, alkylamino, carboxyalkyl, carboxy, and a sulfonamide moiety, and wherein Ry and Rz, independently, are electron donating groups; and,
an agriculturally acceptable carrier,
wherein said agriculturally acceptable carrier is a non-phytotoxic material.

3. An agricultural composition, comprising:
a compound of chemical formula, or a salt thereof, of

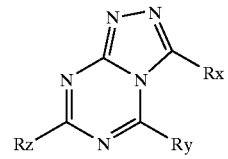

wherein Rx is selected from —NH$_2$, —OH, halogen, alkylamino, carboxyalkyl, carboxy, and a sulfonamide moiety, and
wherein Ry and Rz, independently, are electron donating groups; and,
an agriculturally acceptable carrier,
wherein Rx is —NH$_2$.

4. An agricultural composition, comprising:
a compound of chemical formula, or a salt thereof, of

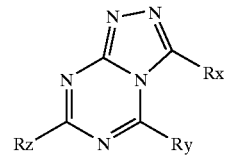

wherein Rx is selected from —NH$_2$, —OH, halogen, alkylamino, carboxyalkyl, carboxy, and a sulfonamide moiety, and
wherein Ry and Rz, independently, are electron donating groups; and,
an agriculturally acceptable carrier,
wherein Rx is a halogen.

5. The agricultural composition of claim 4, wherein Rx is Cl.

6. The composition of claim 1, wherein Ry and Rz, independently, are electron donating groups selected from a lower alkylamino, di-loweralkylamino, amino, hydroxy, carboxy, aryl, lower alkoxy, lower aralkoxy, aryloxy, mercapto and lower alkylthio.

7. The composition of claim 1, wherein Ry and Rz, independently, are electron donating groups selected from —OR, —$CR_AR_BR_C$, —OCOR, —$NR_AR_B$, —SR, wherein R and $R_A$, $R_B$ and $R_C$ are independently selected from an alkyl group and H.

8. The composition of claim 7, wherein R is a $C_1$ to $C_6$ alkyl moiety.

9. The composition of claim 7, wherein R is a $C_1$ to $C_4$ alkyl moiety.

10. The composition of claim 7, wherein R is a $C_1$ to $C_3$ alkyl moiety.

11. The composition of claim 7, wherein R is a $C_1$ alkyl moiety.

12. The composition of claim 7, wherein R and $R_A$, $R_B$ and $R_C$, independently, are selected from H, —$CH_3$, —$CH_2CH_3$, —$CH(CH_3)_2$ and —$CH(CH_2CH_3)_2$.

13. The agricultural composition of claim 3, wherein Ry and Rz, independently, are selected from —$NH_2$, —$CH_3$, —$OCH_3$, —$NHCH_3$, —$N(CH_3)_2$, —$N(CH_3)(CH_2CH_3)$, —$N(CH_2CH_3)_2$, —$NH(CH_2CH_3)$ and —$NH(CH(CH_3)_2)$.

14. A process for producing an agricultural composition, comprising:
forming an agricultural composition comprising a compound of chemical formula, or salt thereof,

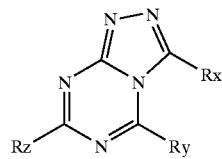

wherein Rx is —$NH_2$, and Ry and Rz, independently, are electron donating groups; and, adding an agriculturally acceptable carrier thereto,
wherein said agriculturally acceptable carrier is a non-phytotoxic material.

15. The process of claim 14, wherein said Rx is selected from COOEt, and —OH.

16. The process of claim 14, wherein said Rx is a sulfonamide substituent.

17. The composition according to claim 1, wherein an effective amount of said compound and said agriculturally acceptable carrier are formulated for application to an agricultural product.

18. The composition of claim 17, wherein said compound and said agriculturally acceptable carrier are a treatment composition, said treatment composition is at least one of an insecticidal, fungicidal and herbicidal treatment.

19. A triazolyl-triazine composition, comprising:
a compound of chemical formula, or salt thereof, represented by a structure of

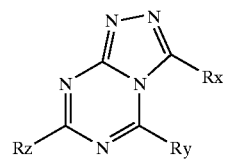

wherein Rx, Ry, and Rz are each a —$NH_2$ moiety; and,
an agriculturally acceptable carrier,
wherein said agriculturally acceptable carrier is selected from at least one of adjuvants, mixers, and enhancers to benefit application of said chemical formula, or said salt thereof.

* * * * *